(12) United States Patent
Riviello

(10) Patent No.: US 8,529,758 B2
(45) Date of Patent: Sep. 10, 2013

(54) CO2-REMOVAL DEVICE AND METHOD

(75) Inventor: John M. Riviello, Los Gatos, CA (US)

(73) Assignee: Dionex Corporation, Sunnyvale, CA (US)

( * ) Notice: Subject to any disclaimer, the term of this patent is extended or adjusted under 35 U.S.C. 154(b) by 276 days.

(21) Appl. No.: 13/069,176

(22) Filed: Mar. 22, 2011

(65) Prior Publication Data

US 2012/0241378 A1 Sep. 27, 2012

(51) Int. Cl.
*B01D 15/08* (2006.01)

(52) U.S. Cl.
USPC ........... 210/198.2; 210/188; 210/656; 422/70

(58) Field of Classification Search
USPC ........ 210/635, 656, 659, 188, 198.2; 422/70; 204/252; 205/748
See application file for complete search history.

(56) References Cited

U.S. PATENT DOCUMENTS

| | | | |
|---|---|---|---|
| 3,897,213 A | 7/1975 | Stevens et al. | |
| 3,920,397 A | 11/1975 | Small et al. | |
| 3,925,019 A | 12/1975 | Small et al. | |
| 5,352,360 A | 10/1994 | Stillian et al. | |
| 5,439,736 A | 8/1995 | Nomura | |
| 6,508,985 B2 | 1/2003 | Small et al. | |
| 7,306,720 B2 * | 12/2007 | Dasgupta et al. | 210/198.2 |
| 7,329,346 B2 | 2/2008 | Liu et al. | |
| 7,585,679 B1 | 9/2009 | Liu et al. | |
| 7,964,411 B2 * | 6/2011 | Dasgupta et al. | 436/161 |
| 2006/0037911 A1 | 2/2006 | Dasgupta et al. | |
| 2006/0057733 A1 | 3/2006 | Liu et al. | |
| 2006/0231404 A1 | 10/2006 | Riviello | |
| 2008/0069731 A1 | 3/2008 | Liu et al. | |
| 2009/0188798 A1 | 7/2009 | Riviello | |
| 2012/0241378 A1 * | 9/2012 | Riviello | 210/656 |

FOREIGN PATENT DOCUMENTS

| | | |
|---|---|---|
| JP | 61 253461 A | 11/1986 |
| WO | WO 03/059822 A2 | 7/2003 |

OTHER PUBLICATIONS

Haddad, P.R. et al. Developments in suppressor technology for inorganic ion analysis by ion chromatography using conductivity detection, *Journal of Chromatograph A* 1000(1-2):725-742 (2003).
Sunden, T. et al. Carbon dioxide permeable tubing for postsuppression in ion chromatography, *Anal. Chem.* 56(7):1085-1089 (1984).
Dionex Corporation, Carbonate Removal Device 200 (CRD 200) for RFIC-EG Systems, 2010.
Dionex Corporation, Carbonate Removal Device 300 (CRD 300) for Carbonate Eluents, 2008.
Ullah, S.M.R., R.L. Adams, K. Srinivasan, P.K. Dasgupta. Asymmetric membrane fiber-based carbon dioxide removal devices for ion chromatography, *Anal. Chem.* 76:7084-7093 (2004).

\* cited by examiner

*Primary Examiner* — Ernest G Therkorn
(74) *Attorney, Agent, or Firm* — David Brezner

(57) ABSTRACT

An electrolytic $CO_2$-removal device for anion analysis of a liquid sample. The device includes a basic chamber and $CO_2$-permeable tubing in the basic chamber. Anion exchange membranes are disposed on opposite sides of the basic chamber, and electrodes are disposed outside the membranes. The device can be integral with a suppressor in an ion chromatography system and/or an aqueous stream purifier. Also, methods performed by the device.

24 Claims, 11 Drawing Sheets

CO2-REMOVAL DEVICE AND METHOD

BACKGROUND OF THE INVENTION

In suppressed ion chromatography ("IC") of anions, aqueous eluent solutions of cation carbonate/bicarbonate and hydroxide herein carbonate/bicarbonate or hydroxide eluents) are most commonly used. Carbonate eluents, which are used primarily in isocratic separations, are suppressed to carbonic acid. Depending on the concentration of the eluent, the conductivity of the suppressed eluent is typical 10-20 µS/cm. The higher background conductivity results in greater noise and reduced analyte intensity (signal) which compromises detection limits. Hydroxide eluents, which are used in both the isocratic and gradient mode, suppress to water, and the background conductivity can be as low as low as 0.2 µS/cm. In practice, background conductivities of suppressed hydroxide are usually in the range of 1-3 µS/cm due to contamination of the eluent with ambient carbon dioxide.

Carbonate eluents typically contain both carbonate ($CO_3^{2-}$) and bicarbonate ($HCO_3^-$). One of the advantages of carbonate eluents is the ease of controlling the ratio of carbonate to bicarbonate, thereby affecting the selectivity of the separation. Unlike hydroxide eluents, where care must be taken to prevent contamination from ambient carbon dioxide, carbonate-based eluents do not suffer from this problem. Many IC stationary phases have been developed for carbonate eluents which take advantage of the monovalent/divalent nature of carbonate eluents.

With hydroxide-based eluents or water used to electrolytically generate hydroxide, the presence of carbon dioxide in the air causes contamination of the eluent. Carbonate contamination of hydroxide eluents compromises the chromatographic separation. Also, the detector response of analyte anions is affected by the increase background conductivity as the result of carbonate. Samples containing carbonate can interfere with the separation and detection of analytes as well. Thus, there is a need in IC for carbonate removal devices.

Dionex Corporation sells two $CO_2$-removal devices, under the CRD 200 and the CRD 300 tradenames. The CRD 200 is used to remove $CO_2$ present in hydroxide eluents and samples and is placed between the suppressor outlet and the conductivity cell inlet. The CRD 300,which offers greater $CO_2$ removal capacity, is used primarily with carbonate eluents and is also placed between the suppressor outlet and the conductivity cell inlet. The CRD 200 and CRD 300 both use a liquid or gas flow stream on the outside of the fiber to remove the carbonic acid as it diffuses from the inside of the fiber to the outside. This liquid or gas flow (regenerant) prevents the accumulation of carbonic acid on the outside of the fiber membrane. The CRD 200 and CRD 300 use either a pumped external chemical regenerant (base) or a vacuum pump to remove the carbonate. The base regenerant promotes the diffusion of the carbonic acid through the fiber membrane since carbonic acid (carbon dioxide) is readily soluble in base. As the base regenerant passes through the decarbonation chamber, the base becomes contaminated with carbonate and is then diverted to waste. Thus, periodic base regeneration is used in this system.

SUMMARY OF THE INVENTION

One embodiment of the invention is an electrolytic $CO_2$-removal device comprising
(a) a basic chamber comprising basic medium comprising an aqueous cation hydroxide solution;
(b) a $CO_2$-permeable barrier which substantially blocks the passage of water, said basic medium being on one side of said $CO_2$-permeable barrier;
(c) a liquid sample stream flow channel on the opposite side of said $CO_2$-permeable barrier from said basic chamber, and having an inlet and an outlet;
(d) a first anion exchange membrane on one side of said basic chamber;
(e) a second anion exchange membrane on the opposite side of said basic chamber from said first anion exchange membrane;
(f) a first electrode on the other side of said first anion exchange membrane from said basic medium; and
(g) a second electrode on the other side of said second anion exchange membrane from said basic medium.

Another embodiment is a method for removing $CO_2$ from an aqueous liquid sample stream, said method comprising
(a) flowing said aqueous liquid sample stream containing $CO_2$ through a liquid sample stream flow channel in an electrolytic $CO_2$-removal device on one side of a $CO_2$-permeable barrier from a basic chamber comprising basic medium comprising an aqueous cation hydroxide solution, said $CO_2$-permeable barrier permitting the passage of $CO_2$ gas but substantially blocking the passage of water; and
(b) passing a current through a first anion exchange membrane on one side of said basic chamber from a cathode on the opposite side of said first anion exchange membrane from said basic chamber, said current passing through said basic chamber and a second anion exchange membrane on the opposite side of said basic chamber from said first anion exchange membrane to an anode on the opposite side of said basic chamber from said second anion exchange membrane, to regenerate said basic medium.

DETAILED DESCRIPTION OF THE PREFERRED EMBODIMENTS

The system of the present invention relates to devices and methods for removing carbon dioxide ($CO_2$) from flowing aqueous liquid streams. In one embodiment, the device is used to remove $CO_2$ from flowing aqueous eluent streams, e.g. carbonate (carbonate/bicarbonate) or hydroxide eluents, including injected samples of analytes to be detected. The analytes comprise a number of ionic species to be determined, particularly anions. Suitable samples include surface waters, and other liquids such as industrial chemical waste, body fluids, beverages and drinking water. When the term "ionic species" is used, it includes species in ionic form and components of molecules which are ionized prior to detection. The $CO_2$-removal device can be used alone or as a section in an integrated device including one or more other sections which perform other functions.

In one embodiment, the $CO_2$-removal device is used in combination with a chromatography apparatus, particularly an ion chromatography apparatus. Ion chromatography systems for anion analysis typically include (a) a chromatography separation column for separating the sample anion ionic species in an eluent, (b) a suppressor through which the effluent from the chromatography column, including separated ionic species, flows, to suppress the eluent, and (c) a detector, typically a conductivity detector including a flow-through conductivity cell, to detect the separated ionic species downstream of the suppressor. When used in an ion chromatography system, the $CO_2$-removal device typically is disposed downstream of the suppressor and upstream of the flow-through conductivity cell of a conductivity detector.

In general, any of the well-known ion chromatography systems, e.g., as illustrated in U.S. Pat. Nos. 3,897,213, 3,920,397, 3,925,019, 3,956,559,or 5,352,360 may be employed.

Figure 1:
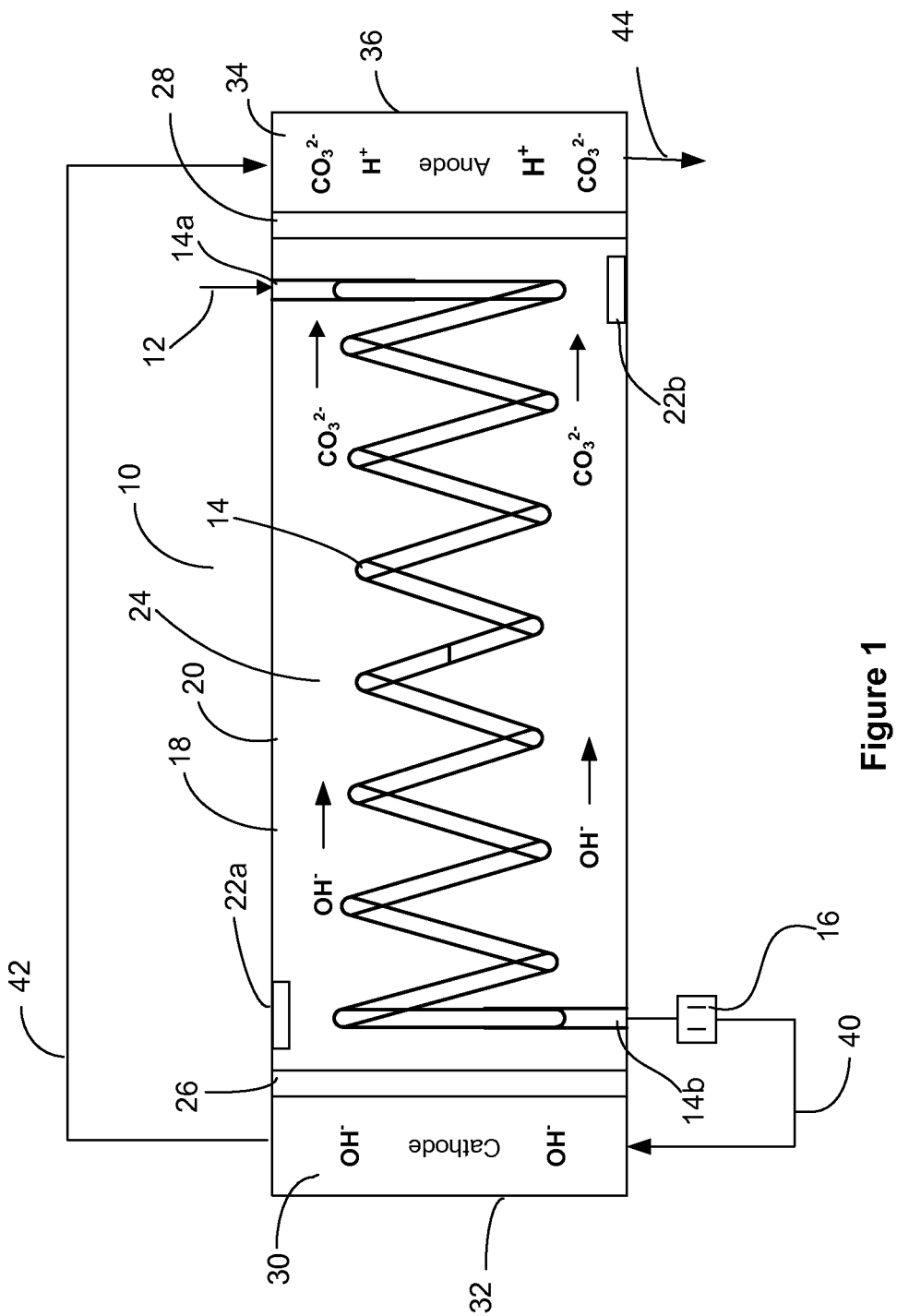
FIG. 1-8 are schematic representations of devices according to the invention.

FIG. 1 schematically illustrates one embodiment of an electrolytic $CO_2$-removal device according to the invention. The $CO_2$-removal device 10 is supplied with a flowing aqueous liquid stream 12 containing $CO_2$ to be removed. In one embodiment, eluent is injected with a liquid sample containing ionic species to be separated in a chromatography separator. Liquid stream 12 is the eluent, containing the ionic species separated in the chromatography column (also referred to as a separator or chromatographic separator). One such eluent contains a mixture of a cation (e.g., sodium or potassium) carbonate/bicarbonate mixture and/or a cation hydroxide. The eluent-containing injected sample flows through a chromatography column, not shown, in which the ionic species are separated. The effluent from the chromatography column flows through a suppressor and then to a detector.

In the embodiment of FIG. 1, stream 12 is the effluent from a suppressor which flows to the $CO_2$-removal device 10 disposed between the suppressor and a detector of an ion chromatography system. Stream 12 is pumped through device 10 using the pump system, not shown, of a typical ion chromatography system. As illustrated in FIG. 1, stream 12 flows through tubing 14 and then to a detector 16, typically through the conductivity cell of a conductivity detector. Device 10 and tubing 14 can similar to the suppressor device described with respect to FIG. 5 of Publication No. US 2006/0057733 A1, published Mar. 16, 2006,with differences in function and structure which will be apparent from the following description. Suppression, or removal of the eluent connection form the aqueous sample stream for anion analysis flowing through said tubing disclosed in the publication, is a totally different method from the $CO_2$-removal method performed in the apparatus of the present invention.

The $CO_2$-permeable barrier in the form of tubing 14 of the present invention functions to remove $CO_2$ from the liquid flowing through the tubing, not cations as in a suppressor. Tubing 14 is a barrier permeable to $CO_2$ but substantially blocks the passage of water, other than possible insignificant leakage, and substantially blocks the passage of analyte ions. The $CO_2$-permeable barrier preferably is highly permeable to $CO_2$ and is not well-adapted for transmitted cations for suppression.

In one embodiment, the $CO_2$-permeable barrier has the permeability for $CO_2$ is described in paragraph 41 of published application US 2006/0037911. In this embodiment "permeability" for the volatile component of interest to be removed from the liquid stream ($CO_2$ gas) in contact with the membrane can be assessed by the fractional removal achieved when a liquid stream containing the said component passes through the $CO_2$ removal device. Such fractional removal is at least 50%, more preferably at least 60%, 70%, 80%, 90% or more. In a preferred embodiment, the removal of a volatile component, e.g., $CO_2$, is greater than 90%, more preferably at least 92, 94, 96, 98%, 99% or more. Percent $CO_2$ removal or reduction can be calculated from the residual background in the case of carbonate or bicarbonate eluent or the residual peak height of the $CO_2$ peak originating from dissolved $CO_2$ in the sample in the case of a hydroxide eluent.

In another embodiment, the permeability to $CO_2$ is as described in paragraph 42 of that publication in which $CO_2$ is the gas of interest. In this embodiment, the permeability of the membrane may be determined by the permeability of the $CO_2$ to be removed in barrers as measured by the method of U.S. Pat. No. 5,439,736,preferably at least 100 barrers, more preferably at least 1,000 barrers, 30,000 barrers, 40,000 barrers or more.

In another embodiment, the $CO_2$-removal barrier is "substantially non-retentive electrostatically for charged ionic species". This term is defined for the outlet only of a membrane suppressor in paragraphs 15 and 16 published application US 2008/0064731 A1. Specifically herein, no substantial amount of charged ionic species would be retained by the barrier. In one embodiment, the barrier in the device is substantially free of ion exchange sites. In another embodiment the barrier has functionally enhanced ion exchange sites of positive and negative charge. In contrast to the publication, not just the outlet but substantially the entire length of the barrier in the $CO_2$-removal device is substantially non-retentive.

The physical dimensions of the tubing of the present invention may be similar to that described in paragraph 17 of the above publication. Thus, tubing 14 may be a "capillary tubing".

Specific suitable materials to be used for tubing 14 are described in Publication No. US 2006/0037911 A1, published Feb. 23, 2006. For example, any of the materials to describe the hollow fibers in paragraphs 3-11 or 33-40 of that publication may be used. Specifically, as described in U.S. Pat. No. 5,439,736,alkylated polysiloxane polymer deposited onto polymeric hollow fibers, porous TTFE tubing (Goretex®), silicone tubing, porous polypropylene tubing coated with silicone, or Teflon AF® gas permeable tubing may be employed. Similarly, the coated materials described in paragraphs 37 through 42 of that publication may be employed.

As illustrated in the embodiment of FIG. 1, the $CO_2$-removal device 10 includes a housing 18, suitably formed of a non-conductive (e.g., plastic) cylindrical column, with flow-through ports including tubing 14 having an inlet 14a and an outlet 14b. The tubing typically projects through liquid tight fittings into and out of housing 18 in direct or indirect fluid communication with the outlet of a chromatography column, not shown. An example of indirect communication would be where a suppressor is disposed between the chromatography column and the tubing inlet 14a. Tubing outlet 14b projects through the housing and is connected to tubing 14 in communication with the inlet of flow-through detector 16, e.g. the conductivity cell of a conductivity detector.

Figure 5:
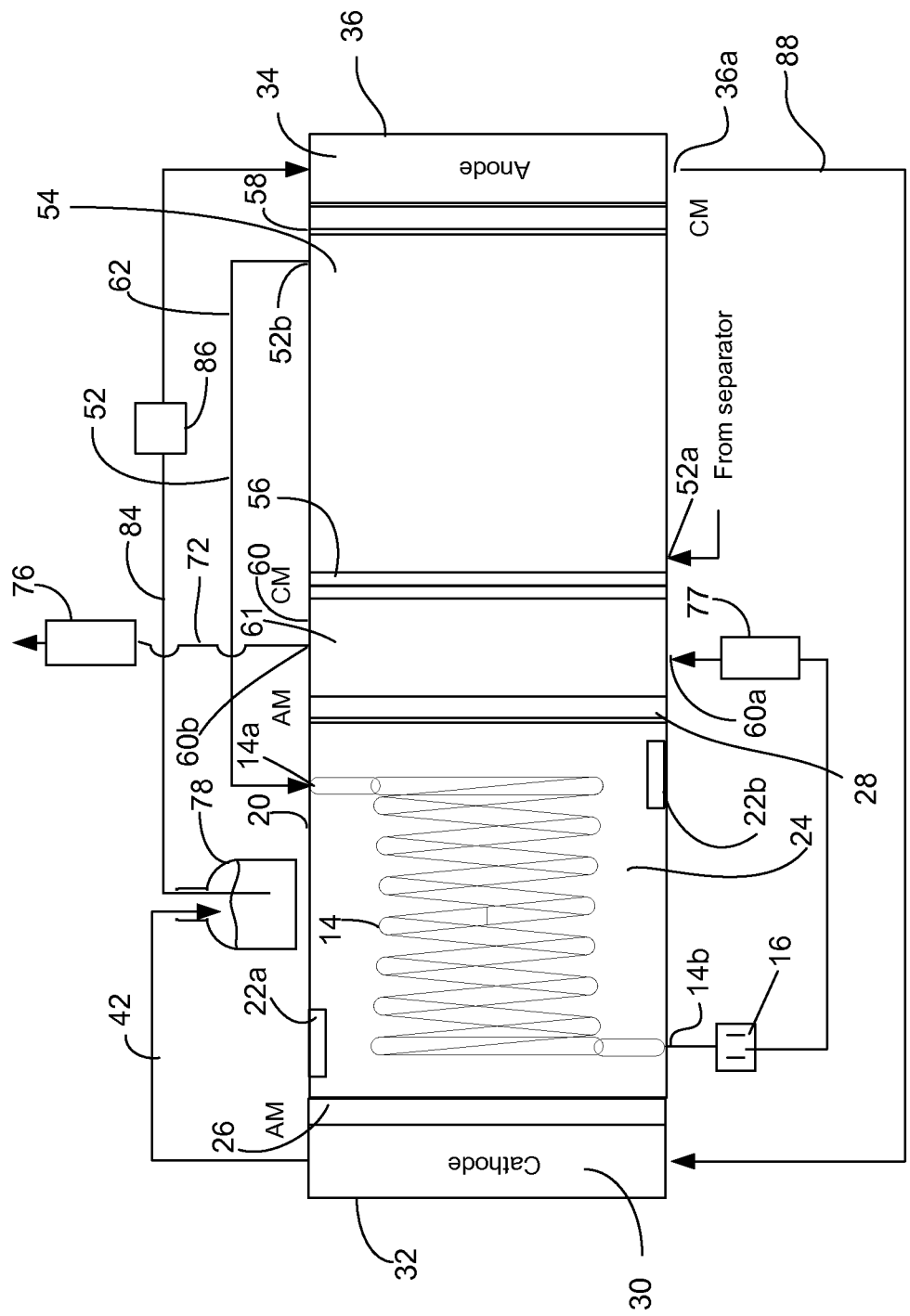

As set forth above, the electrolytic $CO_2$-removal device 10 of the present invention has a general structure similar to that of FIG. 5 of the US 2006/0057733 publication. As illustrated in FIG. 1 herein, device 10 includes a basic chamber 20 on the exterior of the tubing disposed in housing 18.

Basic chamber 20 includes basic medium 24, specifically an aqueous solution of a cation hydroxide, e.g., sodium hydroxide or potassium hydroxide, e.g. at a pH of at least 9,preferably at least 12. The basic medium may also include anion exchange packing formed of material such as described in Publication US 2006/0057733 in a mixture of the solution and packing The cation hydroxide solution bathes the exterior of tubing 14. Housing 10 may include fill ports 22a and 22b to fill chamber 20 with solution and anion exchange material. In one embodiment, the packing material comprises a packed bed of anion exchange particles, typically anion exchange resin. Alternatively, the packing material can be a flow-through monolithic anion exchange packing Preferably, the anion exchange packing and basic solution substantially fills the basic chamber 20 to ensure that the exterior of tubing 14 is bathed with the hydroxide solution. The solution is static or non-flowing during operation.

In a less preferred alternative embodiment, not shown, a solution of cation material such as cation hydroxide, can flow between ports 22a and 22b during operation. The basic medium is on the exterior of the tubing while the liquid sample stream flows through a liquid sample stream flow channel, i.e., the interior of the tubing on the opposite side of the $CO_2$-permeable barrier from the basic chamber.

As illustrated, a first anion exchange membrane 26 is disposed on one side of the basic chamber 20 and spaced-apart second anion exchange membrane 28 is disposed on the opposite side of basic chamber 20 from membrane 26. Thus, basic chamber 20 is defined at its ends (i.e. sides) by membranes 26 and 28 and around its periphery by housing 18, typically in cylindrical form. As used herein, the terms "ion exchange, cation exchange, or anion exchange membranes" are used broadly to define a barrier including ion exchange sites which selectively pass ions of one charge, positive or negative, while substantially blocking the passage of water and ions of opposite charge to the ion exchange sites. Thus, the anion exchange membranes 26 and 28 include exchangeable anions which pass anions but not cations through the wall of tubing 14 to basic medium 24. (This is in contrast to FIG. 5 of US 2006/0057733 which is of opposite polarity, i.e., for anion analysis, the membranes of the publication include exchangeable cations, not anions, and the basic medium also is basic.) This highlights the function of the anion exchange membranes of the present invention which serve the function of passing anions so that anion exchange packing and basic solution can be electrochemically regenerated to maintain the anion exchange packing and basic solution substantially in the hydroxide form (regenerated form) and to provide a means for removal of the carbon dioxide in sample stream 12 which has diffused from through tubing 14 into basic chamber 20.

Basic medium 24 preferably provides continuous contact between anion exchange membranes 26 and 28 to provide a complete electrical path. When used, the anion exchange packing serves several functions. First it acts as a reservoir to retain the removed carbonate. The resin also serves as an electrical conduit for the removed carbonate to electrophoretically flow towards the anode, through the anion exchange membrane and into the anode chamber. The anion exchange resin also provides an electrical conduit for the hydroxide which is produced as the cathode and serves to maintain the anion exchange resin and basic solution "substantially" in the hydroxide form. As illustrated, the basic medium cation hydroxide is static non-flowing during $CO_2$-removal.

For anion analysis, first electrode 30 is in the form of a cathode and is disposed on the other side of anion exchange membrane 26 from the basic medium 24 in basic chamber 20. As illustrated, electrode 30 is disposed in a flow-through electrode chamber 32. Second electrode 34, an anode in the illustrated system, is disposed on the other side of membrane 28 from basic medium 24. As illustrated, electrode 34 is disposed in flow-through electrode chamber 36. The electrodes and their chambers may be of the type described in US 2006/0057733 with respect to FIG. 5 and the Examples in that specification using the device of FIG. 5 and in FIG. 2 of U.S. Pat. No. 6,027,643. It is noted that no external or independent source of aqueous solution is required to flow the solution through chambers 32 and 36 because the effluent from the detector 16 is recycled through the electrode chambers. This also eliminates the need for an additional pump.

Thus, one distinguishing characteristic of the device of FIG. 1 from that of FIG. 5 in US 2006/0057733 is that, for anion analysis, the membrane of that publication are for passing positively charged ions, as illustrated in paragraph 45 of that publication, cation exchange membranes are used in combination with cation exchange medium external to the tubing for anion analysis. Membrane 70 is explicitly disclosed to be cation exchange membrane in FIG. 5, and paragraph 68 of Example 6 describes the construction of that device as using cation exchange membranes.

In the embodiment of FIG. 1, a conduit 40 provides fluid communication between the outlet of detector 16 and the inlet of electrode chamber 32, so that the liquid can flow through chamber 32 out in conduit 42 to recycle through chamber 36 to waste in line 44. This provides a flowing rinse stream in chambers 32 and 36 to carry away the $CO_2$ removed as carbonate or bicarbonate from the system. In a less preferred alternative embodiment, not shown, the flow from detector 16 may be from chamber 36 to chamber 32, i.e., in the reverse direction.

In operation of the device in FIG. 1, aqueous solution 12, typically eluent containing separated analyte ionic species, flows through inlet 14a. $CO_2$ in solution 12 passes across from the interior to the exterior of tubing wall 14 into the basic medium 24 in basic chamber 20 wherein it is converted to carbonate form. Hydroxide ions generated during electrolysis at electrode 30, a cathode for anion analytes, pass across anion exchange membrane 26 into basic medium 24. $CO_2$ passing across the wall of tubing 14 is converted into carbonate ions in basic medium 24. Under the influence of the electric field, carbonate ions in basic medium 24 are drawn towards anode 34, pass across anion exchange membrane 28 into anode chamber 36 and are removed as carbonic acid.

When a DC voltage is applied between electrodes 30 and 34, hydroxide produced at cathode 32 passes through membrane 26 towards anode 34. Under the influence of the electric field, anions present in the basic solution, and anion exchange packing, if present, (primarily hydroxide and carbonate) migrate towards anode 28, pass through membrane 28 and then to anode chamber 34. The anions in chamber 34 are then removed by a liquid flowing stream, which, as illustrated, originates from chamber 30 by recycle. Liquid supplied to electrode chamber 34 typically is suppressed eluent from the detector cell waste in line 40.

The reactions in the electrode chambers 32 and 36 and in basic medium 24 are as follows. In the cathode, water is electrolyzed (reduced) according to the following equation $$2H_2O + 2e^- \rightarrow 2OH^- + H_2$$

In the anode chamber, water is electrolyzed (oxidized) according to the following equation $$H_2O \rightarrow 2e^- + 2H^+ + 1/2 O_2$$

In tubing 14, carbonic acid can dissociate to carbon dioxide and water according to the following equation $$H_2CO_3 \rightarrow CO_2 + H_2O$$

The carbon dioxide can then diffuse through the walls of tubing 14 in to basic medium 24 where the carbon dioxide is converted to carbonate according to the equations $$CO_2 + OH^- \rightarrow HCO_3^-$$

$$HCO_3^- + OH^- \rightarrow CO_3^{2-} + H_2O$$

In another embodiment, not shown, the device of FIG. 1 can be used for the removal of $CO_2$ from a liquid sample prior to injection into an eluent. In this instance, stream 12 is an aqueous liquid sample, and there is no need for detector 16. In this embodiment, it would be desirable to acidify the sample to convert carbonate ion to carbonic acid prior to the flow of the sample into inlet 14a. Such acidification can be performed by passing this liquid sample through a cation exchange device in the hydronium ion form.

The embodiment of FIG. 1 shows eluent solution from a chromatographic separator flowing into tubing 14 of the $CO_2$-removal device. Here, the sole fluid communicating with the $CO_2$-removal device is supplied from the separator outlet.

A number of embodiments will now be described in where the $CO_2$-removal device comprises one section or part of an integral (combined) apparatus for performing $CO_2$-removal in combination with at least an additional section or part performing another function. As used herein, the term "$CO_2$-removal device" refers to such a device by itself or to a $CO_2$-removal section of such a combined or integral device. The terms "$CO_2$-removal device" and "$CO_2$-removal section" will be used interchangeably to describe such a device by itself and/or a section of the combined or integral device.

Figure 2:
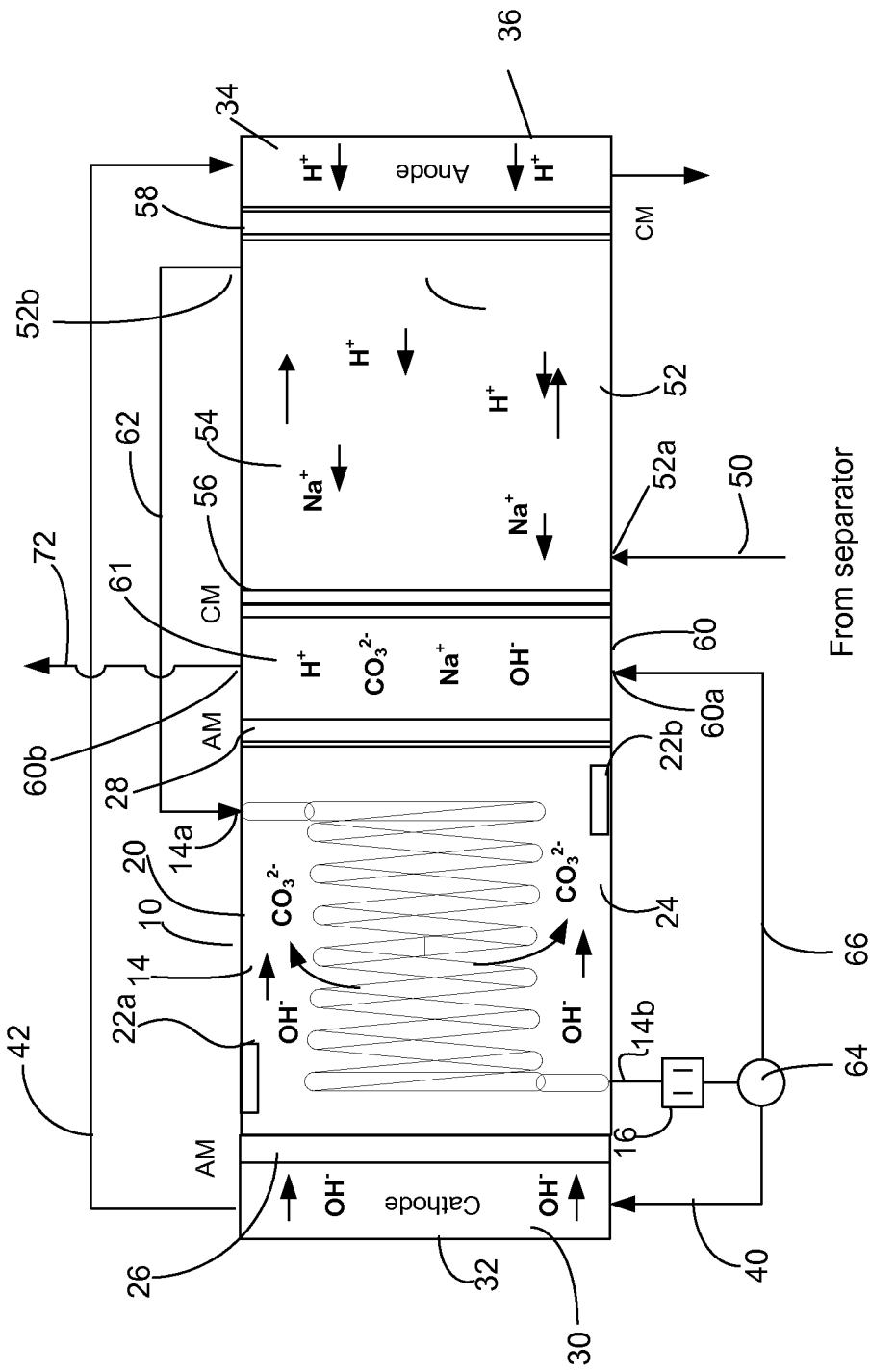

FIG. 2 illustrates one embodiment of such a combined or integrated apparatus which comprises one section, which is a $CO_2$-removal device of the type described with respect to FIG. 1, in combination with a suppressor section. (The terms "combined" and "integrated" will be used interchangeably.) Like part will be designated with like numbers for the $CO_2$-removal device of FIG. 1 and the $CO_2$-removal section of the integrated $CO_2$-removal device/suppressor of FIG. 2. The combined device of FIG. 2 additionally includes a suppressor section and a central flow channel to be described using a different flow pattern. In the embodiment of FIG. 2, flow from the chromatographic separator first is directed into the suppressor section of the device. Thus, the suppressor section will be described first.

Referring specifically to FIG. 2, an aqueous solution 50, specifically an eluent, containing analyte ionic species, e.g. previously separated in a chromatography separator, flows into an inlet 52a of suppressor section 52 which comprises cation exchange medium 54, suitably packing Suppressor section 52 also includes spaced first and second cation exchange membranes 56 and 58, respectively, flanking opposite side of ion exchange medium 54. Electrode 34 is on the other side of membrane 58 from cation exchange medium 54 in suppressor section 52. Electrode 34 also is on the other side of anion exchange membrane 28 from basic medium 24 in $CO_2$-removal section 20. Here, the number 10 refers to both the independent self-contained $CO_2$-removal device of FIG. 1 and the $CO_2$-removal section in FIG. 2. Medium 54 can be any of the known flow-through ion exchange media used in suppressors of the prior art. Thus, cation exchange medium 54 can comprise a cation exchange resin packed bed or a flow-through cation exchange monolith.

Central flow channel 60 is defined by the space between anion exchange membrane 28 and cation exchange membrane 56. Central flow channel 60 further comprises ion exchange medium 61 and has an inlet 60a and an outlet 60b. The function of the ion exchange medium 61 is to maintain a continuous electrical connection between cation exchange membrane 56 and anion exchange membrane 28 and allows for a flow path through central flow channel 60 for removal of eluent counter ions and carbonate. The ion exchange medium 61 is compromised of flow-through ion exchange material and can be anion exchange, cation exchange or a mixture or anion and cation exchange. Like suppressor cation exchange medium 54, ion exchange medium 61 can be in a form such as a packed bed of ion exchange resin or a flow-through monolith. Any of the foregoing ion exchange materials listed are suitable because the applied electric field will result in eluent cations (Na+ or K+), hydroxide and carbonate migrating into the central flow channel.

In the embodiment of FIG. 2, the aqueous liquid stream 50 enters suppressor section 52 through inlet 52a and exit through outlet 52b. As illustrated, outlet 52b is connected to inlet 14a of tubing 14 by conduit 62. Tubing outlet 14b is connected to detector 16 as in FIG. 1 and from there to the inlet of electrode chamber 32 by conduit 40 as in FIG. 1. However, in contrast to FIG. 1, the device of FIG. 2 includes a mixing tee or a splitter valve 64 which directs one portion of the effluent from detector 16 through conduit 40 and another portion of the detector effluent through conduit 66 to inlet 60a of central flow channel 60. Thus, as illustrated, the outlet of the sample stream flow channel in the interior of tubing 14a is in fluid communication with the inlet of detector 16, and the detector outlet is in fluid communication with electrode 30 in chamber 32. Also, in FIG. 2, electrode 30 is a cathode in operation and is in fluid communication with electrode 34 (an anode in operation) through conduit 42.

In the embodiment of FIG. 2, suppression is performed by suppressor section 52 integrated into the device. Thus, aqueous liquid stream 50 may be connected directly to the outlet of a chromatographic separator, not shown, without external suppression and could comprise an eluent including analyte ionic species previously separated in a chromatographic separator. As is well known, such eluent could include a cation (sodium or potassium) carbonate/bicarbonate eluent, a cation hydroxide such as sodium or potassium hydroxide, or a mixture of them. During operation of the device of FIG. 2, the eluent from the chromatographic separator flows through inlet 52a of suppressor section 52. There, the eluent counter-ions to the analyte, e.g., sodium or potassium, are retained on the cation exchange medium. Under the influence of the electrical field applied between cathode 30 and anode 34, the eluent cations pass through cation exchange membrane 56 to central flow channel 60. Hydronium ions produced at anode 34 pass into cationic exchange medium 54 through cation exchange membrane 58 to substantially regenerate ion exchange medium 54. Cation exchange membranes 56 and 58 are the same general type as anion exchange membranes 26 and 28 except that the exchangeable ions are of opposite charge.

The eluent suppressed in suppressor section 52 flows out outlet 52a through conduit 62 to inlet 14a of tubing 14 in carbon-dioxide removal section 10. Exterior to tubing 14 in basic chamber 20 is the basic medium 24 of the type described above which is continuously regenerated by hydroxide produced at cathode 30 flowing across anion exchange membrane 26 drawn toward anode 34 through the basic medium 24. The terms "ion exchange packing" and "ion exchange medium" are used interchangeably herein. The reactions which occur in suppressor section 54 are generally the same as in a packed bed electrolytic suppressor, e.g. as disclosed in U.S. Pat. No. 6,508,985.

In the illustrated device, recycle is accomplished by splitting the effluent or waste from detector 16 and directing it both to the central flow channel 60 and to electrode 30 in electrode chamber 32 (a cathode in the embodiment of FIG. 2). However, in a less preferred embodiment, the flow between the electrode chambers could be reversed. The flow from electrode chambers 32 and central flow channel 60 can be balanced by adjusting the pressure drop through the flow paths. This can be accomplished by using small bore tubing. Water for the anode and cathode chambers preferable is substantially ion-free to prevent ions from being drawn into the suppressor section 52 and $CO_2$-removal section 10. In the device of FIG. 2, when a DC voltage is applied between the electrodes, electrolysis of water occurs in both the anode and the cathode. Anode 34 is the source of hydronium ions for suppression in suppressor section 52.

The flow of ions in the embodiment of FIG. 2 is illustrated for a system which includes eluent (e.g., sodium carbonated/sodium bicarbonate) from the chromatography separator fed to inlet 52a of suppressor section 52. Thus, the $OH^-$ ions produce at cathode 30 pass through anion exchange membrane 26 into the basic medium 24. The carbon dioxide which passes from the interior of tubing 14 into basic medium 24 is converted to carbonate ion which flows across anion exchange membrane 28 under the influence of the electric field between cathode 30 anode 34. Hydronium ions generate at anode 34 pass through cation exchange membrane 58 into suppressor section 52 to regenerate cation exchange medium therein. Sodium ions from the eluent in suppressor section 52 pass through cation exchange membrane 56 into central flow channel 60, wherein the sodium ions are converted to sodium carbonate/sodium bicarbonate and pass to waste in line 72.

In a typical operation of the device of FIG. 2, a carbonate/bicarbonate eluent from an anion separator is directed to the inlet of the suppression section 52 in which the sodium or potassium carbonate/bicarbonate solution is converted to carbonic acid. The analyte anions are converted to the acid form. Under the influence of the applied DC electric field, the eluent cation migrates through the cation exchange medium in section 52 towards the cathode. When the eluent cation reaches the cation membrane 56 of central flow channel 60, the eluent cation passes through cation membrane 56 and into central flow channel 60 where a flow of liquid removes the eluent cation. Hydronium, electrolytically produced at anode 34, passes through cation exchange membrane 58 into suppression section 52 and continues to migrate towards cathode 32. The electrolytically produced hydronium keeps the cation exchange medium 54 of suppression section 52 regenerated.

The liquid flow from suppression section outlet 52b is directed to tubing inlet 14a. The suppressed eluent (carbonic acid) passes through the interior of tubing 14 resulting in the diffusion of carbon dioxide through the tubing wall and into the medium 24 in which the carbon dioxide is present as carbonate. With a DC electric field applied, carbonate electrophoretically migrates towards anode 34. When the carbonate reaches membrane 28, the carbonate passes through membrane 28 and into central flow channel 60 where a flow of liquid removes the carbonate. Hydroxide, electrolytically produced at cathode 30, passes through membrane 26 into medium 24 and continues to migrate towards anode 34. Thus, the electrolytically-produced hydroxide keeps basic medium 24 continuously regenerated. The liquid flowing out tubing outlet 14b is directed through detector 16. Thus, the liquid stream is split to direct a portion of the flow to the central flow channel 60 to remove the eluent cations and carbonate, while the other portion of the stream is directed to cathode chamber 32 to anode chamber 36 and then to waste. Splitting of the stream prevent electrolytic gases from passing through central flow channel 60.

Figure 3:
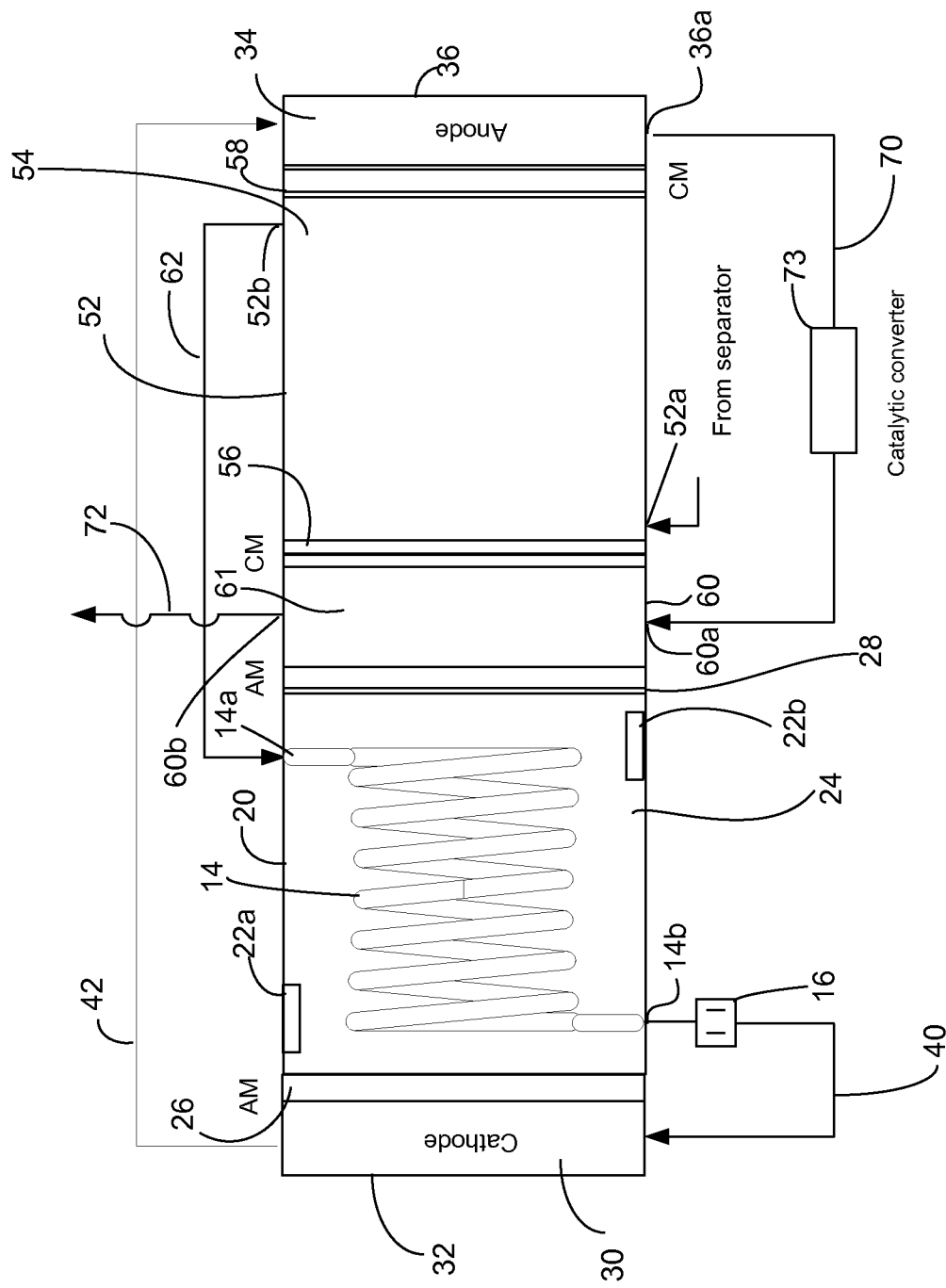

Referring to FIG. 3, another embodiment of an integrated or combined apparatus is illustrated which includes a $CO_2$-removal device in one section and a suppressor device in another section. Like parts will be designated with like numbers for the embodiments of FIGS. 2 and 3. In the embodiment of FIG. 3, all flow from detector 16 is through conduit 40 to electrode (cathode) 30 in electrode (cathode) chamber 32. In this embodiment, the flow to inlet 60a of central flow channel 60 is from anode 34 in chamber 36 through outlet 36a into conduit 70, and inlet 60a of central flow channel 60. Thus, the flow is from the outlet of detector 16 through cathode chamber 32 to anion chamber 36 through central flow channel 60 and from there to waste in line 72. In this embodiment, a device 73 is provided for removal of the hydrogen and oxygen gases generated during electrolysis in the electrode chambers prior to passing back through central flow chamber 60. One embodiment of the device comprises a catalytic gas elimination device illustrated in U.S. Pat. No. 7,585,679 which converts hydrogen and oxygen gases to water. Other known devices to remove the gases include de-gasser such as a vacuum de-gasser. Alternatively, back pressure can be applied to the central flow channel outlet to keep the electrolytic gases (oxygen and hydronium) in solution.

Figure 4:
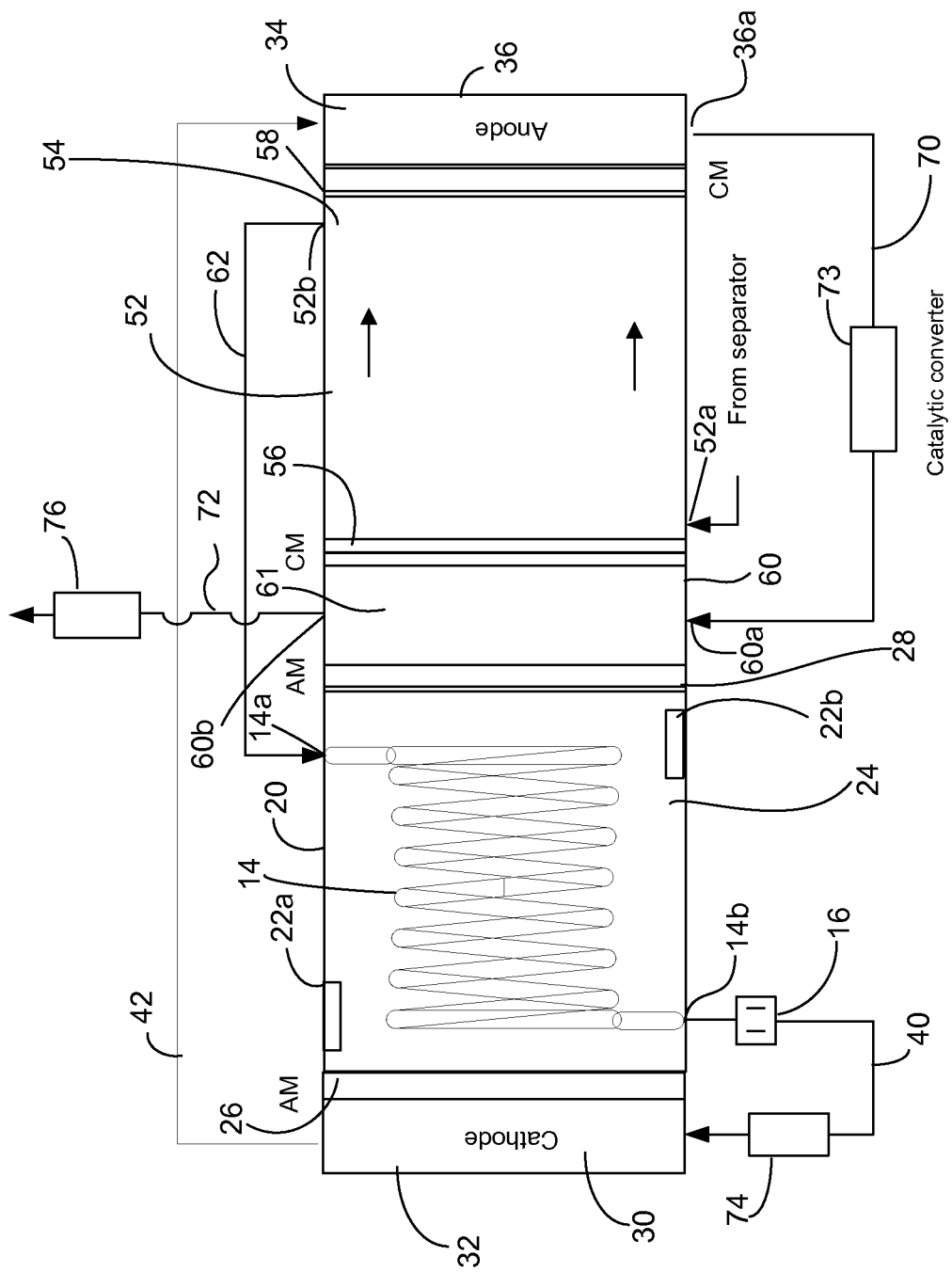

Another embodiment of an integrated or combined suppressor and $CO_2$-removal device according to the invention is illustrated in FIG. 4. This device is similar to that of FIG. 3 except that it is adapted to purify the solution exiting central flow channel 60 in line 72 to form all or part of the eluent solution to be directed to the chromatography separator. This recycle employs the principles and flows of eluent recycle or eluent regeneration as described in U.S. Pat. Nos. 7,329,346, and 7,585,679 and US App. 2009 0188798. The device includes an anion trap 74 in line 40 between detector 16 and electrode chamber 32. A suitable anion trap including anion exchange resin and is sold by Dionex Corporation under the name TAC-2 (trace anion concentrator-2). The device of FIG. 4 also includes a cation trap 76 in line 72 of a conventional type such as a packed bed of cation exchange resin such as sold by Dionex Corporation under the name CTC-1 (cation trap column-1). The solution exiting cation trap 76 includes recycled eluent sodium or potassium carbonate/sodium bicarbonate and/or sodium or potassium hydroxide which has been purified to a sufficient extent to be used as an eluent for the sample to be separated by a chromatography separator. Thus, the eluent in conduit 72 can be recycled for use as the eluent source for the eluent and sample flow to the chromatography separator.

Referring to FIG. 5, another embodiment is illustrated of a combined device including a $CO_2$-removal section and a suppressor section similar to that of FIG. 4 for eluent recycle. Like parts will be designated with like numbers. Here, a separate water source 78 is employed. The effluent from detector 16 flows through anion trap 77 into central flow channel 60 (instead of into cathode chamber 32 as illustrated in FIG. 4). The solution flows from central flow channel 60 through outlet 60b through conduit 76 to cation trap 76 and is recycled as an eluent source. Here, water from an external water source 78 flows through conduit 84 under influence of pump 86 into anion chamber 36 and in conduit 88 back to cathode chamber 32. This configuration uses separate water source 78 for the electrode rinse solution which is recycled. This eliminates the use of a device for removing the oxygen and hydrogen gases generated during electrolysis.

Figure 6:
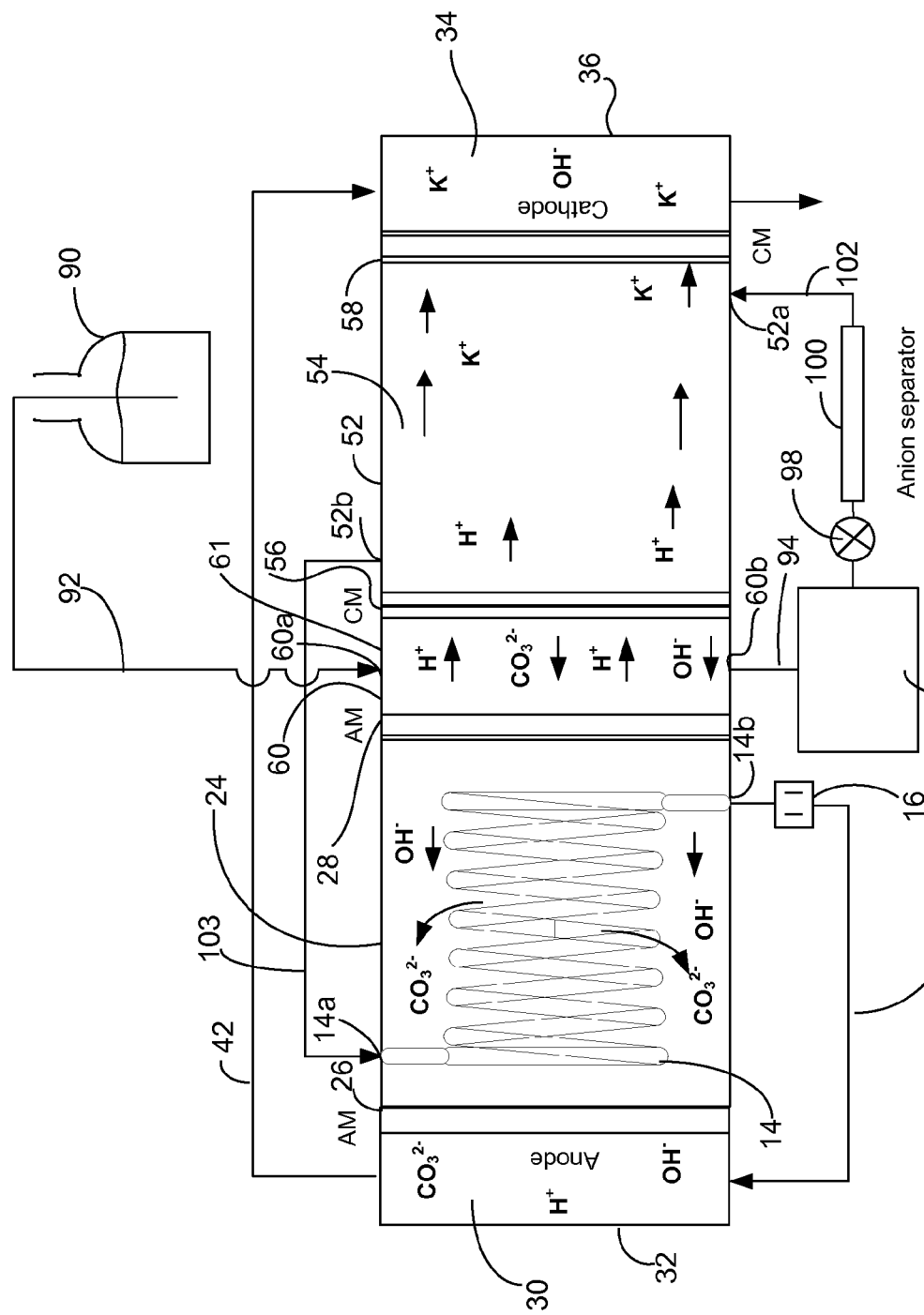

FIG. 6 illustrates an integrated device including a $CO_2$-removal section, a suppressor section, and a central flow channel. The device of FIG. 6 is similar to the devices of FIGS. 2-5; however the polarity is reversed. Like parts will be designated with like numbers. Here, the external plumbing and devices external to the integrated device are different. The integrated device additionally performs the function of water purification for eluent generation. Specifically, it includes water source 90 (e.g. deionized water) which flows in conduit 92 to the inlet 60a of central flow channel 60 and through outlet 60b in conduit 94 to electrolytic eluent generator 96 (e.g., the type described in U.S. Pat. No. 7,153,476). A liquid sample, including ionic species to be separated, is injected in sample injector 98 into the eluent exiting generator 96 and flows through anionic separator 100 from there in conduit 102 into inlet 52a of suppressor section 52. The eluent exits suppressor section 52 in outlet 52b and flows in line 103 to tubing inlet 14a. Solution exiting tubing outlet 14b flows through detector 16 and is recycled in conduit 40 to electrode chamber 32. Here, electrode 30 is an anode and electrode 24 is a cathode. Thus, the polarity of the system in FIG. 6 is reversed in comparison to that of FIG. 5. The device performs three functions: water purification for water supplied to an electrolytic eluent generator, suppression, and carbon dioxide removal. In this embodiment, the central flow channel medium 60 deionizes and polishes the water supplied to electrolytic eluent generator 96. After passing through eluent generator 96, the polished water with the injected sample flow to separator column 100. Contaminant ions in water source 90, including carbonate, can be removed in central flow channel medium 60 under the influence of the electric field apply between anode 30 and cathode 34. The effluent waste solution from detector 16 is recycled for use as the electrode rinse solution directed to electrode chamber 32 and 36.

Figure 7:
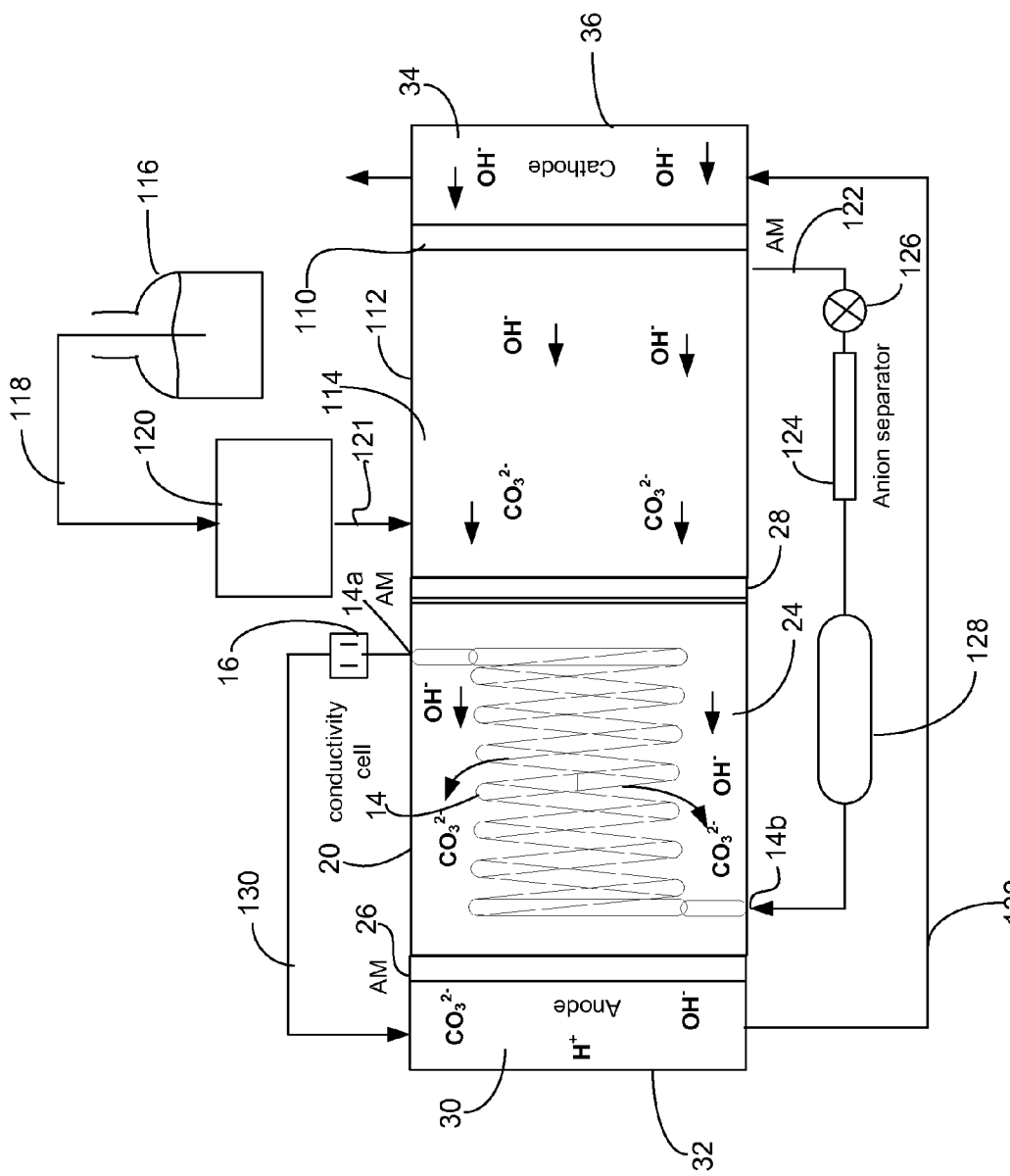

Referring to FIG. 7, a $CO_2$-removal device is used as a section of an integrated apparatus which include a $CO_2$-removal section and an electrolytic aqueous stream (e.g. aqueous eluent) purifier section. In this device, the suppressor is external to the integrated device. Like parts will be designated with like numbers for the $CO_2$-removal section of FIG. 2.

Referring specifically to FIG. 7, a third anion exchange membrane 110 is spaced from the second anion exchange membrane 28 on the opposite side of membrane 28 from basic medium 24. An aqueous stream purifying section 112 is defined by the space between anion exchange membranes 28 and 110. Purifying section 112 further comprises aqueous stream purifying ion exchange medium 114 dispose in the space between membranes 28 and 110. Here, electrode 34 (a cathode) in electrode chamber 36 is disposed on the other side of anion exchange membrane 110 from aqueous purifying anion exchange medium 114.

As illustrated in FIG. 7, the device contains only three (anion) exchange membranes. Moreover, there are only two chambers to the interior of the electrode chambers 32 and 36 in this device, in contrast to the three-chamber integrated devices of FIGS. 2-6. Further, the polarity of the electrodes is reversed from that in FIGS. 1-5. Thus, in this device, electrode 30 is an anode while electrode 34 is a cathode. As illustrated, the aqueous stream to be purified includes eluent, e.g, in the form of a cation hydroxide such as potassium or sodium hydroxide, which is generated externally to the integrated device. Here, the integrated device is an electrolytic eluent purifier in combination with a $CO_2$-removal device used as part of an ion chromatography system which includes an electrolytic eluent generator between a water source and the purifier. The eluent generator, chromatographic separator, and suppressor are external to the integrated device, as will be described below.

Referring again to FIG. 7, purified water such as deionized water from a reservoir 116 is directed in line 118 to an electrolytic eluent generator 120 of the foregoing type. The eluent stream is directed in line 121 to the inlet of purifier section 112 and flows through purifier section medium 114, through line 122 to anion separator 124. Sample is injected in sample injector 126. After separation of the sample ionic species in separator 124, the eluent flows through external electrolytic suppressor 128 such as the type sold by Dionex Corporation under the designation ASRS (anion self-regenerating suppressor), and into the inlet 14a of tubing 14 in the $CO_2$-removal device section 20 of the type described above.

The purifier ion exchange medium 114 includes exchangeable anions, suitably a flow-through bed of anion exchange resin or a monolith with anion exchange sites. A preferable anion exchange medium is high capacity anion exchange resin such as Dowex 1×8 (hydroxide form) or high capacity anion exchange monolith such as that used in the Dionex Cation Atlas suppressor. The anion exchange medium serves to retain and remove contaminate anions, including carbonate. Contaminant anions and carbonate can originate in the water source 116 or from the eluent generator and compromise chromatographic analysis. Removing contaminant anions from the eluent before the injection valve results in improved chromatography. The solution exits tubing 14 and is detected by detector 16, suitably the conductivity cell of a conductivity detector. The waste effluent from detector 16 can flow in a recycle line 130 to rinse electrode (anode) 30 in electrode chamber 32. After passing through chamber 32, the solution can also be used to rinse cathode 34 in chamber 36 by flowing in on line 132 to chamber 36. Alternatively, in a less preferred embodiment, the flow from detector 16 may be reversed so that it flows to chamber 36 prior to flowing to chamber 32.

In the embodiment of FIG. 7, the suppressor is external to the integrated $CO_2$-removal and eluent purifier device. Also, the eluent at purifying section 112 operates on the high pressure side of the electrolytic eluent in generator 120, so that purifying section 112 can have a pressure rating that exceeds the operating pressure of the anion separator 124. In operation, hydroxide ions generated at electrode (cathode) 34 flow across anion exchange membrane 110 into purifier section 112. The eluent purifier section 112 removes trace anionic purities from the electrolytically generated eluent. At the anode 30, hydronium ion is produced by the electrolysis of water. The hydronium pairs with hydroxide or trace anions that are migrating from the purifier section 112 and the $CO_2$ removal section 20. Substantially all carbonate that is present in the eluent, either from injected sample or from ambient $CO_2$ absorbed by the basic eluent, will be removed in the purifier section 20.

Figure 8:
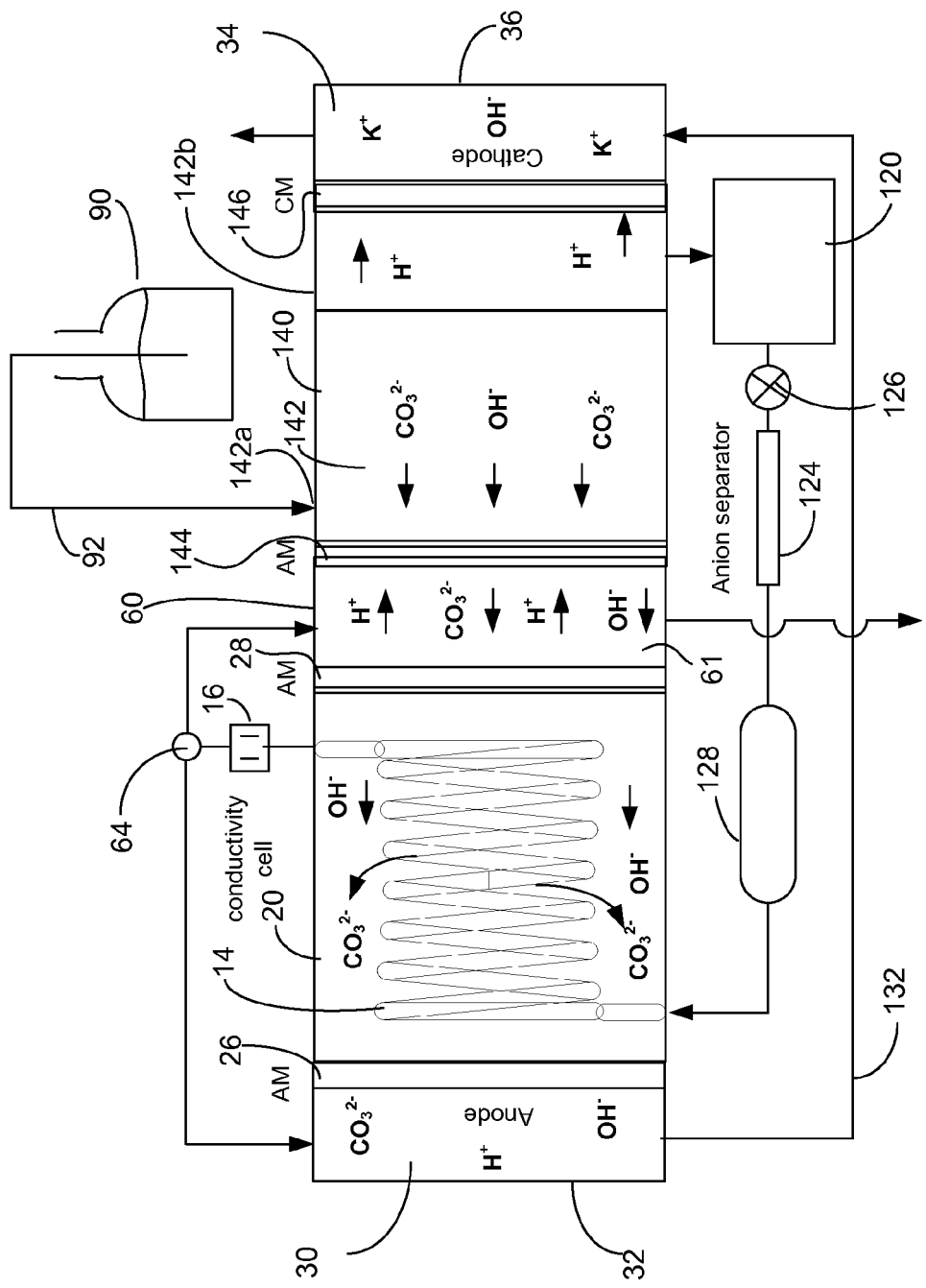

In another embodiment, illustrated by FIG. 8, an electrolytic water purifying section is combined with a $CO_2$-removal section in an integrated device. Like parts with the foregoing figures will be designated with like numbers for the systems of FIGS. 6, 7 and 8. Here the deionized water from reservoir 90 flows in line 92 to a water purifying section 140 including water purifying ion exchange medium 142. A third anion exchange membrane 144 is disposed on the other side of anion membrane 28 from $CO_2$-removal section 20 and is spaced from membrane 28. The space between membranes 28 and 144, central flow chamber 60, is filled with ion exchange medium 61 such as mixed or composite ion exchange resin. Medium 61 contains both anion and cation exchanges packing and serves as a source of hydronium and hydroxide produced by water splitting. The generated hydroxide passes through anion exchange membrane 28 and serves to regenerate basic medium 24. Hydronium ion produced in medium 61 acts as the counter ions for contaminant anions removed from purifying section 140 through anion exchange membrane 144.

Water purifying section 140 is defined on one side by anion exchange membrane 144 and on the other side by spaced cation exchange membrane 146. Electrode (cathode) 34 in electrode chamber 36 is disposed on the opposite side of cation exchange membrane 146 from water purifying section 140.

The water purified in section 140 flows to eluent generator 120, which generates hydroxide eluent. Sample is injected at sample injector 126 downstream from eluent generator 120. The generated eluent flows into anion separator 124 to external suppressor 128 of the type described with respect to FIG. 7. After flow through suppressor 128, the solution flows into tubing 14 in $CO_2$-removal section 20 and from there to detector 16.

After flow through detector 16, the waste solution can be split by tee 64 so that one portion flows as a rinse solution past electrode 30 in chamber 32, and from there in line 132 as a rinse for electrode 34 and chamber 36. As with respect to FIG. 7, in a less preferred embodiment, the direction of flow through the electrode chambers can be reversed.

Here, water purifying section 140 further purifies water from source 90. The purifier medium 142 can contain only anion exchange resin, but preferably also contains cation exchange resin to contain contaminant cations. The ion exchange medium 142 serves to remove trace ionic contaminants from the feed water used for electrolytic eluent generation. In one embodiment, the ion exchange medium 142 is at least partially anionic. It may contain a layer of anion exchange medium 142a at the inlet of section 140 adjacent to membrane 144 and also adjacent to a layer of mixed or composite ion exchange material 142b disposed towards the outlet of section 140. A mixed resin is typically a mixture of anion and cation exchange material where the anion to cation capacity ratio of the mixture is approximately 1:1. A composite ion exchange medium is mixture of anion and cation exchange material where the capacity ratio is greater than or less than 1. Typical ratios for a composite mixture are greater than 1.2 or less than 0.8 (anion to cation capacity ratio). A layer of anion exchange medium 142a at the inlet of purifying section 140 improves removal of anionic species. Cationic species are removed in a second medium layer 142b towards the outlet of purifying chamber 140. Layer 142b of mixed or composite ion exchange material near the outlet enhances removal of cationic species and also produces hydronium and hydroxide (via water splitting) to regenerate the anion exchange and mixed/composite layer. In another embodiment, the medium 142 may be anion exchange, mixed or a composite of anion and cation exchange material.

Advantages of the foregoing system include the combination into a single device of either a $CO_2$-removal device and a suppressor or of a $CO_2$-removal device and an eluent or water purifier or combinations thereof. The device can be used with carbonate and hydroxide eluents.

In order to further illustrate the present invention, the following non-limiting examples are provided.

EXAMPLE 1

Removal of $CO_2$ from a Suppressed Carbonate Eluent Using the Device of FIG. 1

An electrolytic carbon dioxide removal device as shown in FIG. 1 was constructed using machined high density polyethylene hardware to retain the electrodes, membranes and resin. The machined body had an internal bore with a diameter of 0.95 cm and a length of 3.8 cm. This cavity defined the basic chamber (or decarbonation chamber). The body was threaded externally on each end allowing internally threaded end caps to terminate the body. Each end of the body had a female ¼-28 fitting perpendicular to the bore which connected the decarbonation chamber to the outside of the body. A cylindrical tubing sleeve was constructed from XN-5340 extruded polypropylene netting (Industrial Netting, Inc, Minneapolis, Minn.). The tubing sleeve was approximately 0.6 cm in diameter and 3.2 cm in length. A 150 cm length of 300 µm id×420 µm od silicone coated polypropylene tubing (CRD tubing, Dionex Corp., Sunnyvale, Calif.) was wrapped around the tubing sleeve and the ends of the tubing were inserted through the ¼-28 fitting through hole so to bring the tubing ends to the exterior of the body. The CRD tubing ends were then inserted into 5 cm of 0.020"×0.062" Tefzel tubing to sleeve the CRD tubing allowing the tubing to be connected to standard chromatography fittings. Threaded bolts and ferrules were attached to each end of the Tefzel tubing which sealed the CRD tubing into Tefzel sleeve and machined body.

Platinum electrodes were placed in each end cap. Anion exchange membranes (Electropure Excellion I-200 anion membrane—hydroxide form, a product of SnowPure Inc, San Clemente, Calif.) were placed in direct contact with the electrodes forming the anode and cathode chambers. The anode chamber end cap assembly was then threaded to the body. The decarbonation chamber was filled with anion exchange resin (DOWEX™ 1×4-200 mesh, a product of the Dow Chemical Company, Midland, Mich.) in the hydroxide form. Sodium hydroxide (0.25M) was then added drop wise to fill the decarbonation chamber. Finally, the cathode chamber end cap assembly was threaded on the opposite end of the body to seal the decarbonation chamber.

Figure 9:
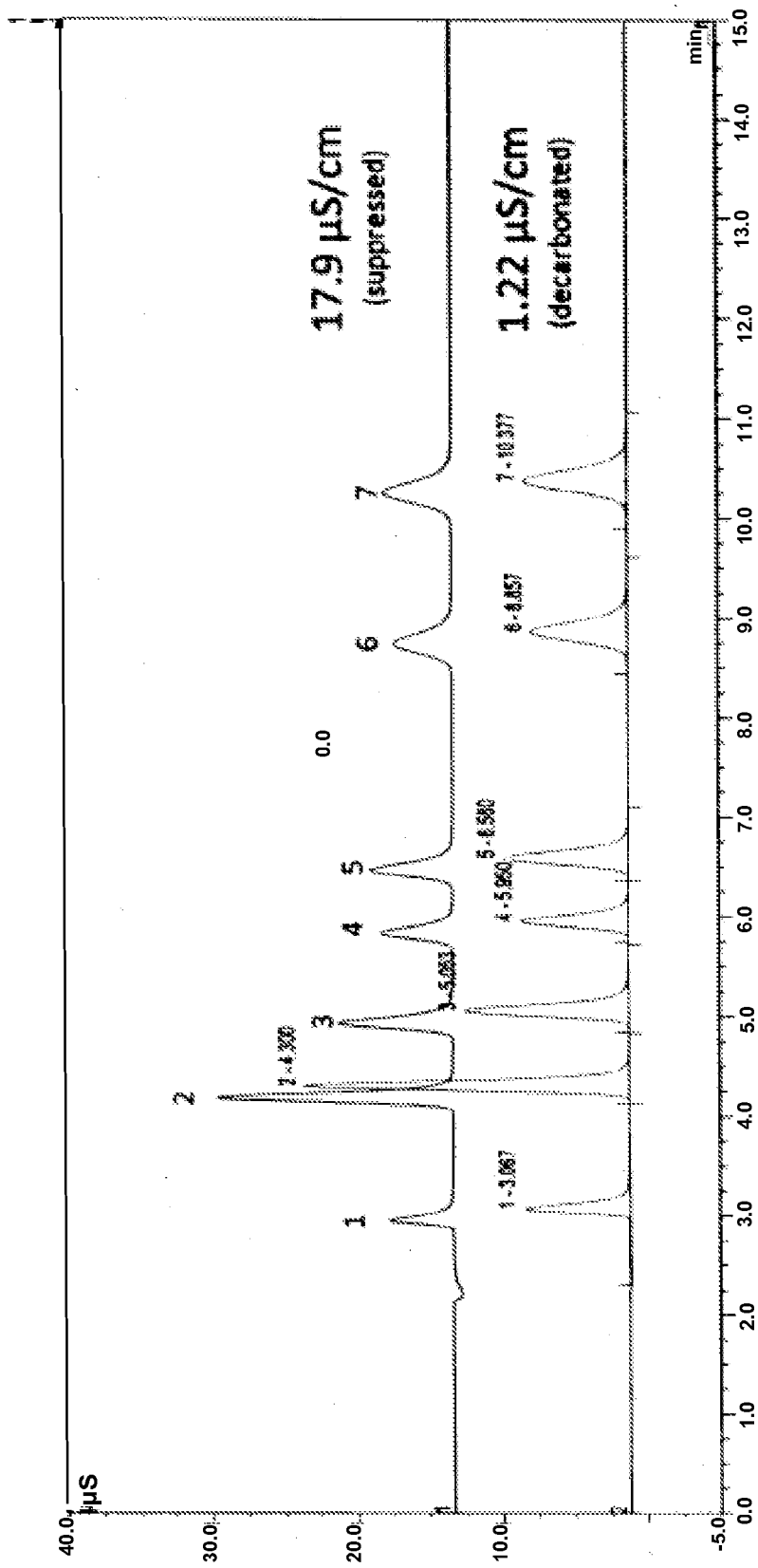
FIG. 9-11 depict experimental results illustrating the present invention.

The device of FIG. 1 was tested using a Dionex DX500 Ion Chromatography system (a product of Dionex Corp, Sunnyvale, Calif.) consisting of a GP50 pump, two CD25 conductivity detectors and a LC30 chromatography oven. The injection valve was fitted with a 20 µL loop and a anion standard (Table I) was injected. An eluent of 4.5 mM sodium carbonate and 1.4 mM sodium bicarbonate was pumped at a flow of 1.2 mL/min to a analytical anion exchange column (AG22/AS22 a product of Dionex Corp., Sunnyvale, Calif.) and then to a Dionex ASRS-300 electrolytic suppressor. A first conductivity cell was placed at the eluent outlet of the ASRS. From the first conductivity cell, the suppressed eluent was connected to the inlet (anode end) of the electrolytic $CO_2$ acid removal device described above. The eluent flow from the device outlet was directed to the second conductivity cell. The second conductivity cell outlet flows to the device cathode chamber, then the anode chamber and finally to the ASRS regenerant in and to waste. An Agilent E3611A DC power supply (Agilent Corp., Santa Clara, Calif.) was used to power the device of FIG. 1 at a constant current of 50 mA (approximately 30V). FIG. 9 is a chromatogram of a seven anion standard obtained with the system above. The background conductivity from the suppressor was 17.9 µS/cm. After passing through the device, the background conductivity decreased to 1.22 µS/cm. This represents a 93.2% reduction in the background conductivity.

Figure 10:
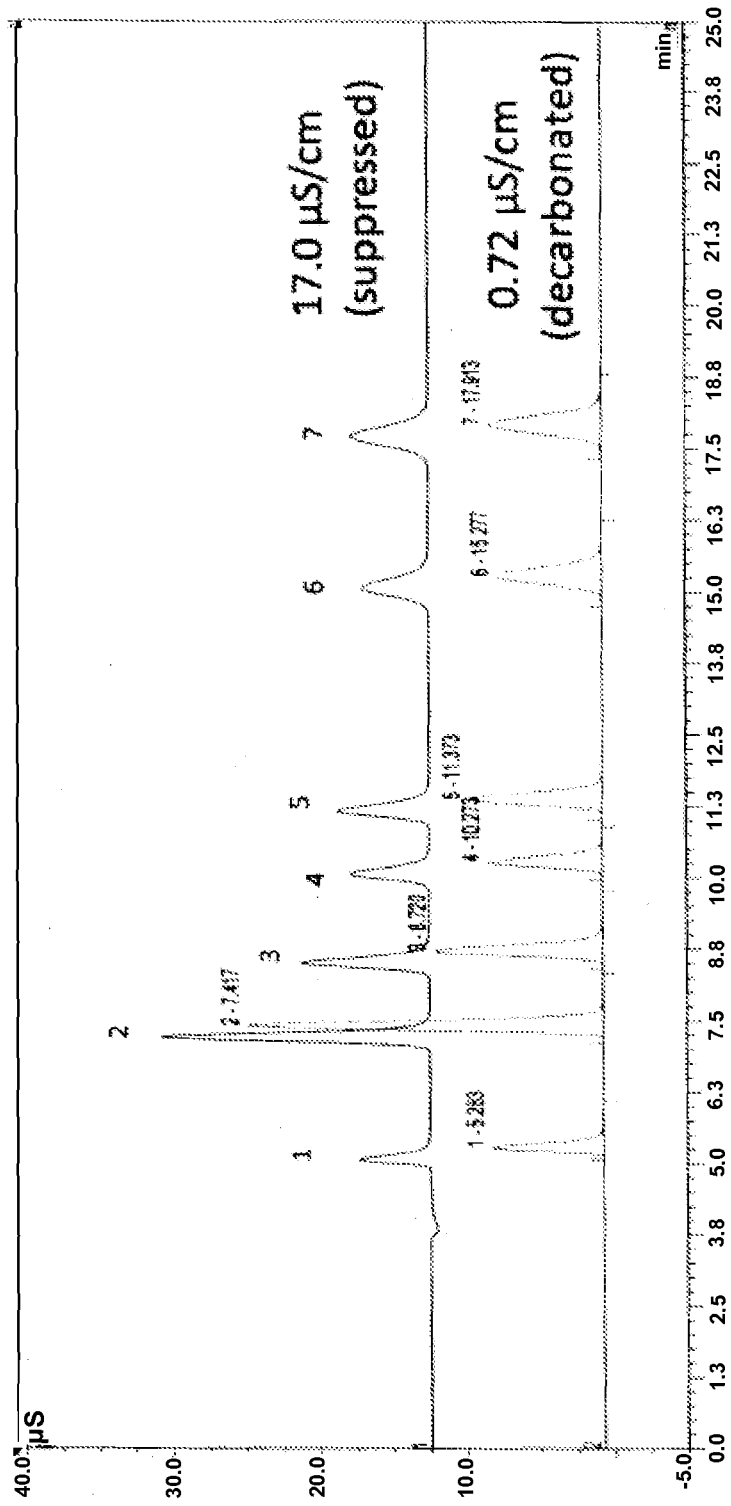

The system of FIG. 1 was used to generate the chromatograms of FIG. 10 by decreasing the flow rate to 0.60 mL/min. At the lower flow rate, the background conductivity from the suppressor decreased from 17.0 to 0.72 µS/cm, representing a 95.8% reduction in the background conductivity. The lower flow rate increases residence time in the decarbonation tubing which result in improved carbon dioxide removal compared to the higher flow rate.

TABLE I

| Number | Analyte | Concentration (mg/L) |
|---|---|---|
| 1 | $F^-$ | 2 |
| 2 | $Cl^-$ | 10 |
| 3 | $NO_2^-$ | 10 |
| 4 | $Br^-$ | 10 |

TABLE I-continued

| Number | Analyte | Concentration (mg/L) |
|---|---|---|
| 5 | $NO_3^-$ | 10 |
| 6 | $PO_4^{3-}$ | 20 |
| 7 | $SO_4^{2-}$ | 10 |

EXAMPLE 2

Removal of $CO_2$ Using the Device of FIG. 1

In this example, deionized water was pumped directly to the first conductivity cell (no separator column or suppressor). The measured conductivity of the deionized with the first conductivity cell was 0.82 uS/cm. From the first conductivity cell, the water was then directed to the inlet of the device of FIG. 1. The measured conductivity at the second cell was 0.23 µS/cm demonstrating the ability of the FIG. 1 device to remove carbon dioxide from deionized water.

EXAMPLE 3

CO2 Removal and Suppression Using the Integrated Electrolytic Suppressor and Carbon Dioxide Removal Device of FIG. 2

An integrated electrolytic anion suppressor and carbon dioxide-removal device as shown in FIG. 2 was constructed using machined high density polyethylene hardware. The device consisted of two bodies, a coupler to connect the bodies and two end caps. The coupler had a through hole of diameter of 0.95 cm and the depth of the through hole was 0.95 cm. The coupler also had two ¼-28 female fittings allowing liquid flow through the coupler. One body was constructed as the decarbonation chamber as described in Example 1, except that the end cap used to form the anode chamber was replaced with a coupler. The coupler contained an anion exchange membrane on the decarbonation chamber side. The coupler was filled with cation exchange resin (DOWEX™ 50×4-200 mesh, a product of the Dow Chemical Company, Midland, Mich.) in the hydronium form. On the suppressor chamber side of the coupler a cation exchange membrane exchange membrane (Electropure Excellion I-100 cation exchange membrane, a product of SnowPure Inc, San Clemente, Calif.) was placed. Next, the second body (suppressor section) was attached to the coupler and the body filled with cation exchange resin (DOWEX™ 50×4-200 mesh, a product of the Dow Chemical Company, Midland, Mich.). A cation exchange membrane was placed on the anode chamber side of the suppression chamber body. A platinum electrode (anode) was placed in the anode end cap and the end cap attached to the suppression chamber body.

Figure 11:
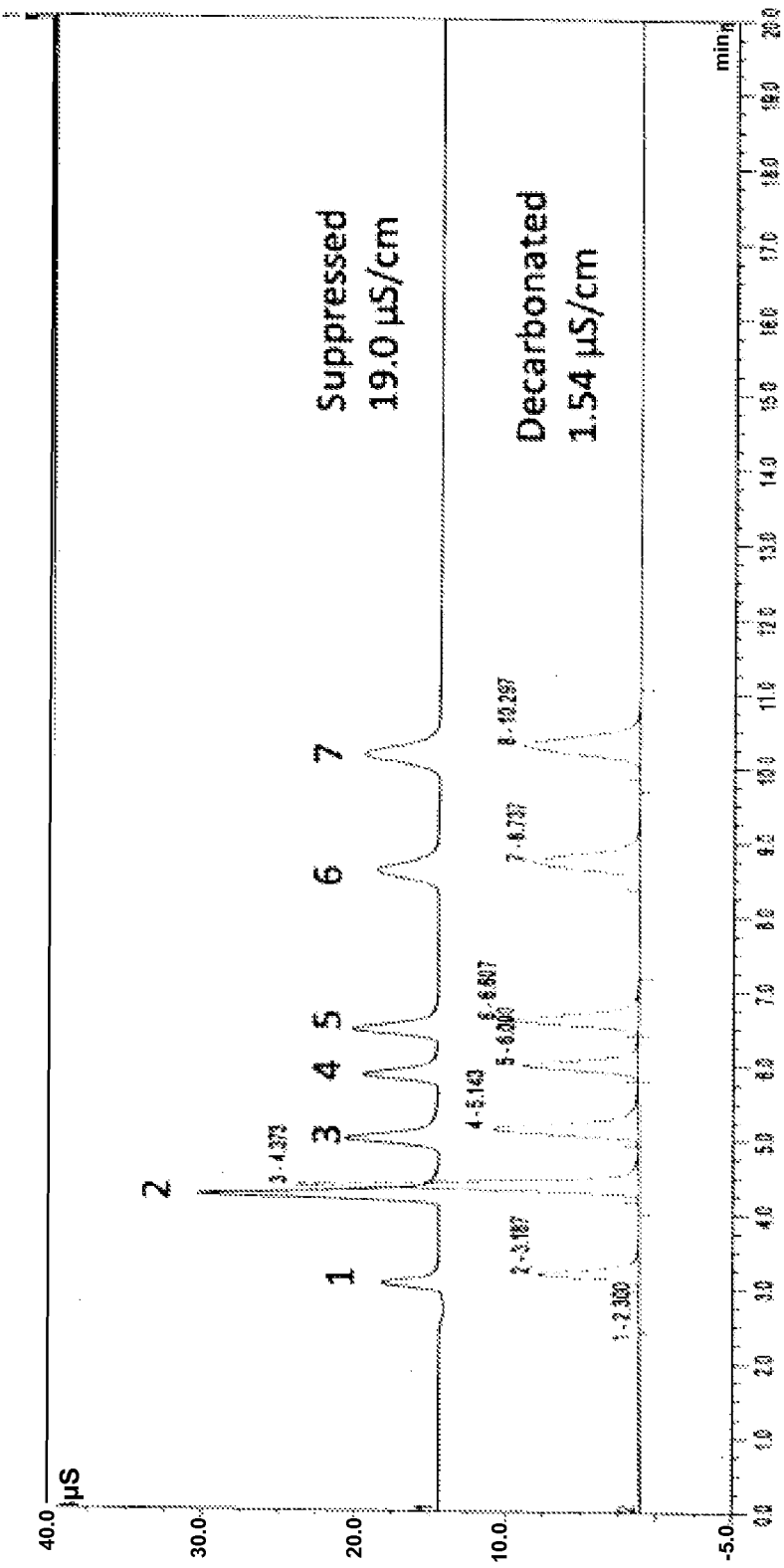

The device of FIG. 2 was tested using a Dionex DX500 Ion Chromatography system (a product of Dionex Corp, Sunnyvale, Calif.) consisting of a GP50 pump, two CD25 conductivity detectors and a LC30 chromatography oven. An eluent of 4.5 mM sodium carbonate and 1.4 mM sodium bicarbonate was pumped at a flow of 1.2 mL/min to a analytical anion exchange column (AG22/AS22 a product of Dionex Corp., Sunnyvale, Calif.). From the analytical column, the flow was directed to the inlet of the suppressor section. A first conductivity cell was placed at the eluent outlet of the suppressor section of the device of FIG. 2. From the first conductivity cell, the suppressed eluent was then directed to the inlet of the $CO_2$-removal section chamber and then to the second conductivity cell. From the second conductivity cell, the flow is split (via a tee) and directed to the cathode chamber and the central flow chamber (coupler). The flow from the cathode chamber passes through the anode chamber and then to waste. An Agilent E3611A DC power supply (Agilent Corp., Santa Clara, Calif.) was used to power the device of FIG. 2 at a constant current of 40 mA (approximately 50V). FIG. 11 is a chromatogram of a seven anion standard obtained with the system above. The background conductivity from the suppression chamber was 19.0 µS/cm and after passing through the decarbonation chamber, the background conductivity decreased to 1.54 µS/cm representing a 91.9% reduction in the background conductivity.

What is claimed is:

1. An electrolytic $CO_2$-removal device comprising
    (a) a basic chamber comprising basic medium comprising an aqueous cation hydroxide solution;
    (b) a $CO_2$-permeable barrier which substantially blocks the passage of water, said basic medium being on one side of said $CO_2$-permeable barrier;
    (c) a liquid sample stream flow channel on the opposite side of said $CO_2$-permeable barrier from said basic chamber, and having an inlet and an outlet;
    (d) a first anion exchange membrane on one side of said basic chamber;
    (e) a second anion exchange membrane on the opposite side of said basic chamber from said first anion exchange membrane;
    (f) a first electrode on the other side of said first anion exchange membrane from said basic medium; and
    (g) a second electrode on the other side of said second anion exchange membrane from said basic medium.

2. The removal device of claim 1 in which said basic medium further comprises anion exchange packing 3. The removal device of claim 1 in which said $CO_2$-permeable barrier is capable of removing at least 90% of the $CO_2$ in a liquid stream containing $CO_2$ flowing through said sample stream flow channel.

4. The removal device of claim 1 in which said $CO_2$-permeable barrier is substantially non-retentive electrostatically for charged ionic species.

5. The removal device of claim 1 in which said $CO_2$-permeable barrier comprises tubing, said liquid sample stream flow channel comprises the interior of said tubing, and said basic chamber comprises a chamber exterior to said tubing and in contact therewith.

6. The removal device of claim 1 in a liquid chromatographic system further comprising a liquid chromatography separator having an inlet and an outlet, said separator outlet being in fluid communication with said liquid stream flow channel inlet.

7. The removal device of claim 6 further comprising
    (h) first and second electrode chambers in which said first and second electrodes are disposed; and
    (i) a detector having an inlet and outlet, said liquid sample stream flow channel being in fluid communication with said detector inlet, and said detector outlet being in fluid communication with said first electrode chamber.

8. The removal device of claim 7 in which said first electrode chamber is in fluid communication with said second electrode chamber.

9. The removal device of claim 7 in which the fluid communication from said separator outlet to said liquid stream flow channel is the sole fluid source communication with said removal device.

10. The removal device of claim 6 further comprising a suppressor, having an inlet and an outlet, said suppressor inlet being in fluid communication with said separator outlet and said suppressor outlet being in fluid communication with said liquid sample stream flow channel.

11. An integrated combined apparatus comprising the removal device of claim 1 in one section and a suppressor in another section, said combined apparatus further comprising
- (h) a suppressor section comprising cation exchange packing and spaced first and second cation exchange membranes flanking opposite sides of said cation exchange packing;
- (i) a central flow channel defined by space between said second anion exchange membrane and said first cation exchange membrane, further comprising ion exchange medium, and having an inlet and an outlet, said second electrode being disposed on the other side of said second cation exchange membrane from said cation exchange packing.

12. The combined apparatus of claim 11 in combination with a detector having an inlet and an outlet, said sample stream flow channel outlet being in fluid communication with said detector inlet through a first conduit and said detector outlet being in fluid communication with said first electrode.

13. The combined apparatus of claim 12 in which said first electrode chamber is in fluid communication with said second electrode chamber.

14. The combined apparatus of claim 12 in which said detector outlet is in fluid communication with said central flow channel.

15. The combined apparatus of claim 12 in a liquid chromatography system further comprising a liquid chromatography separator having an inlet and an outlet, said separator outlet being in fluid communication with said suppressor section.

16. The combined apparatus of claim 11 in which said $CO_2$-permeable barrier is substantially uncharged on its sample stream flow channel side.

17. The combined apparatus of claim 11 in which said second electrode is in fluid communication with said central flow channel inlet through a second conduit.

18. The combined apparatus of claim 17 further comprising a gas removal device disposed in the second conduit.

19. The combined apparatus of claim 12 further comprising an ion exchange trap disposed in line between said detector and said first electrode chamber.

20. The combined apparatus of claim 11 in which said $CO_2$-permeable barrier comprises tubing, said liquid sample stream flow channel comprises the interior of said tubing, and said basic chamber comprises a chamber exterior to said tubing and in contact therewith, said detector outlet being in fluid communication with said central flow channel inlet through a third conduit.

21. The combined apparatus of claim 20 further comprising an ion exchange trap in said third conduit.

22. The combined apparatus of claim 11 in combination with a water source, an eluent generator having an inlet and an outlet and a chromatography separator having an inlet and an outlet, said water source being in fluid communication with said central flow channel inlet, said central flow channel outlet being in fluid communication with said eluent generator inlet, said eluent generator outlet being in fluid communication with said separator inlet and said separator outlet being in fluid communication with said suppressor section cation exchange packing.

23. A combined apparatus comprising the $CO_2$-removal device of claim 1 and an aqueous stream purifier device, said combined apparatus further comprising
- (h) a third anion exchange membrane spaced from said second anion exchange membrane on the opposite side of said second anion exchange membrane from said basic chamber;
- (i) a central flow channel defined by the space between said second and third anion exchange membranes further comprising ion exchange medium;
- (j) a cation exchange membrane spaced from said third anion exchange membrane; and
- (k) a aqueous stream purifier section defined by the space between said third anion exchange membrane and said cation exchange membrane, said aqueous stream purifying section further comprising aqueous stream purifying ion exchange medium disposed in said last named space, said second electrode also being disposed on the other side of said cation exchange membrane from said aqueous stream purifier section.

24. A combined apparatus comprising the $CO_2$-removal device of claim 1 and an aqueous stream purifier device, further comprising
- (h) a third anion exchange membrane spaced from said second anion exchange membrane on the opposite side of said second ion exchange membrane from said basic medium; and
- (i) an aqueous stream purifying section defined by the space between said second and third anion exchange membranes, said aqueous stream purifying section further comprising aqueous stream purifying ion exchange medium disposed in said last named space, said second electrode also being on the other side of said third anion exchange membrane from said aqueous stream purifying anion exchange medium.

* * * * *